(12) United States Patent
Kim et al.

(10) Patent No.: US 10,061,180 B2
(45) Date of Patent: Aug. 28, 2018

(54) PHOTON GENERATOR USING FREQUENCY COMB AND NANOPLASMONIC TECHNOLOGY AND GENERATING METHOD THEREOF

(71) Applicant: Max Planck POSTECH/Korea Research Initiative, Gyeongsangbuk-do (KR)

(72) Inventors: Dongeon Kim, Gyeongsangbuk-do (KR); Seungchul Kim, Busan (KR)

(73) Assignee: MAX PLANCK POSTECH/KOREA RESEARCH INITIATIVE, Gyeongsangbuk-Do (KR)

( * ) Notice: Subject to any disclaimer, the term of this patent is extended or adjusted under 35 U.S.C. 154(b) by 0 days.

(21) Appl. No.: 15/486,622

(22) Filed: Apr. 13, 2017

(65) Prior Publication Data

US 2018/0157148 A1   Jun. 7, 2018

(30) Foreign Application Priority Data

Dec. 6, 2016   (KR) ........................ 10-2016-0164815

(51) Int. Cl.
| | |
|---|---|
| *G02F 1/35* | (2006.01) |
| *G01N 21/552* | (2014.01) |
| *G02B 5/00* | (2006.01) |
| *B82Y 20/00* | (2011.01) |

(52) U.S. Cl.
CPC ........... *G02F 1/353* (2013.01); *G01N 21/553* (2013.01); *G02B 5/008* (2013.01); *B82Y 20/00* (2013.01); *G02F 2203/10* (2013.01); *G02F 2203/15* (2013.01); *G02F 2203/56* (2013.01); *Y10S 977/781* (2013.01)

(58) Field of Classification Search
CPC .. G02F 1/353; G02F 2203/10; G02F 2203/15; G02F 2203/56; G02B 5/008; G01N 21/553; B82Y 20/00; Y10S 997/781
See application file for complete search history.

(56) References Cited

U.S. PATENT DOCUMENTS

| | | | | |
|---|---|---|---|---|
| 8,488,639 | B1 * | 7/2013 | Diels | H01S 3/10092 |
| | | | | 372/13 |
| 8,780,948 | B2 * | 7/2014 | Wilkinson | H01S 3/1303 |
| | | | | 372/18 |
| 9,746,748 | B2 * | 8/2017 | Vampa | G02F 1/353 |
| 2014/0112360 | A1 * | 4/2014 | Telle | H01S 3/1394 |
| | | | | 372/28 |

(Continued)

FOREIGN PATENT DOCUMENTS

JP   2013072848 A   4/2013

OTHER PUBLICATIONS

Kim et al., "High-Harmonic Generation by Resonant Plasmon Field Enhancement", Nature, vol. 453, Jun. 5, 2008, pp. 757-760.*

(Continued)

*Primary Examiner* — Daniel Petkovsek
(74) *Attorney, Agent, or Firm* — Dinsmore & Shohl LLP

(57) ABSTRACT

Provided is a photon generator. The photon generator includes a frequency comb generator configured to generate a frequency comb of a predetermined frequency band, and a controller configured to perform frequency locking for frequency stabilization of an optical frequency generated by the frequency comb generator.

17 Claims, 7 Drawing Sheets

(56) References Cited

U.S. PATENT DOCUMENTS

2016/0087395 A1* 3/2016 Wanke ............... H01S 5/1096
372/22
2017/0187161 A1* 6/2017 Fermann ............ H01S 3/1112

OTHER PUBLICATIONS

Geng, Xiao Tao et al., Frequency comb transferred by surface plasmon resonance, Nature Communications, Feb. 22, 2016, 7 pages, Issue 7.

* cited by examiner

PHOTON GENERATOR USING FREQUENCY COMB AND NANOPLASMONIC TECHNOLOGY AND GENERATING METHOD THEREOF

CROSS-REFERENCE TO RELATED APPLICATION

This application claims the benefit of Korean Patent Application No. 10-2016-0164815, filed on Dec. 6, 2016, in the Korean Intellectual Property Office, the disclosure of which is incorporated herein in its entirety by reference.

STATEMENT REGARDING PRIOR DISCLOSURE BY THE INVENTOR OR A JOINT INVENTOR UNDER 37 C.F.R. § 1.77(b)(6)

Geng et al, *Frequency comb transferred by surface plasmon resonance* (hereinafter "Geng reference"), was published on Feb. 22, 2016, which is less than one year prior to the effective filing date of the present application, Oct. 6, 2016. A copy of the Geng reference is provided on a concurrently filed Information Disclosure Statement pursuant to the guidance of 78 Fed. Reg. 11076 (Feb. 14, 2013). Co-authors Dongeon Kim and Seungchul Kim invented and conceived of the inventive subject matter disclosed in the Geng reference. Co-authors Xiao Tao Geng, Byung Jae Chun, Ji Hoon Seo, Kwanyong Seo, Hana Yoon, and Young-Jin Kim did not invent or conceive of any of the inventive subject matter captured in the Geng reference. These co-authors acted either in a support capacity or under instruction by Dongeon Kim and Seungchul Kim.

BACKGROUND

1. Field

One or more embodiments relate to photon generating apparatuses and methods using a frequency comb and nanoplasmonic technology, and more particularly, to photon generators and photon generating methods using a surface plasmon resonance and a frequency comb stabilized to an atomic clock.

2. Description of the Related Art

Nanoplasmonics may refer to a phenomenon in which electrons move at a frequency equal to the frequency of light, as a collective movement of intra-metal free electrons that occurs when light or laser is incident on a structure in which a particular condition or pattern is engraved on a particular metal such as gold, silver, or copper. Using this, even without the magnitude of a strong electric field required in a dielectric medium, the movement of electrons in a solid medium may be controlled very rapidly and accurately.

A surface plasmon may be a collective behavior of electrons vibrating at the speed of light, in which the light may be spatially controlled with accuracy of nanoscale below wavelength. Also, since additional laser field amplification may be performed by a plasmon resonance phenomenon, the flow of stronger electrons may be controlled even with the same laser energy and an electron pulse signal controlled and emitted by the waveform of light may be generated on a solid surface. Also, since the induction characteristics of a surface plasmon phenomenon change very sensitively to a refractive index change of a material, it may be applied to optical refractive index measurement technology. For this reason, it is utilized in various and extensive fields such as bio/nano sensors, nonlinear optical researches, optical computers, and optical communications.

SUMMARY

One or more embodiments are to greatly improve the accuracy of various conventional sensor measurement technologies by combining a technology of inducing a surface plasmon and a technology of applying a stabilized optical frequency technology to a plasmonic technology by using an optical frequency stabilized to an atomic clock.

Also, one or more embodiments are to provide a photon generator including an apparatus for inducing a surface plasmon by using a stabilized optical frequency and a sensor including the same.

Also, one or more embodiments are to utilize an optical frequency in a high-accuracy standard measurement technology by locking a laser or optical frequency based on an atomic clock having high stability and accuracy.

Also, one or more embodiments are to apply to biosensors, surface plasmon resonance (SPR) sensors, and other standard optical measurement technologies by greatly improving the frequency stability of surface plasmonics by utilizing an optical frequency stabilized to an atomic clock for surface plasmon induction.

Objects of the inventive concept are not limited to the above-mentioned objects, and unmentioned other technical objects may be clearly understood from the following description by those of ordinary skill in the art.

Additional aspects will be set forth in part in the description which follows and, in part, will be apparent from the description, or may be learned by practice of the presented embodiments.

According to one or more embodiments, a photon generator includes: a frequency comb generator configured to generate a frequency comb of a predetermined frequency band; and a controller configured to perform frequency locking for frequency stabilization of an optical frequency generated by the frequency comb generator.

Also, the photon generator may further include a surface plasmon resonance generator configured to generate a surface plasmon resonance state of the frequency comb. Herein, the surface plasmon resonance generator may include a nanohole array film having a nanohole array structure including a plurality of nanoholes. Also, the nanohole array film may include a metal layer formed on a substrate, and the metal layer may include a plurality of circular holes.

Also, the metal layer may include gold, and the substrate may include a quartz layer coated with indium tin oxide. Also, a diameter of the circular hole may be 150 nm to 250 nm, and a pitch between the plurality of circular holes may be 500 nm to 550 nm. Also, a thickness of the metal layer may be 80 nm to 120 nm, and a thickness of the substrate may be 20 nm to 30 nm.

Also, the controller may be configured to frequency-lock the optical frequency generated by the frequency comb generator to an atomic frequency standard. Herein, the controller may include an atomic clock.

According to one or more embodiments, a photon generating method includes: generating a frequency comb of a predetermined frequency band; and frequency-locking an optical frequency to an atomic frequency standard for frequency stabilization of the optical frequency generated by a frequency comb generator.

Also, the photon generating method may further include generating a surface plasmon resonance state of the frequency comb by a surface plasmon resonance generator. Herein, the generating of the surface plasmon resonance state may include the frequency comb passing through a nanohole array film having a nanohole array structure including a plurality of nanoholes.

Also, the nanohole array film may include a metal layer formed on a substrate, and the metal layer may include a plurality of circular holes. Also, the metal layer may include gold, and the substrate may include a quartz layer coated with indium tin oxide. Also, a diameter of the circular hole may be 150 nm to 250 nm, and a pitch between the plurality of circular holes may be 500 nm to 550 nm. Also, a thickness of the metal layer may be 80 nm to 120 nm, and a thickness of the substrate may be 20 nm to 30 nm.

Also, the frequency comb may be reconverted from a surface plasmonic mode to a photonic mode after being converted from the photonic mode to the surface plasmonic mode by the surface plasmon resonance generator.

Also, according to one or more embodiments, a biosensor includes a photon generator having the above features.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
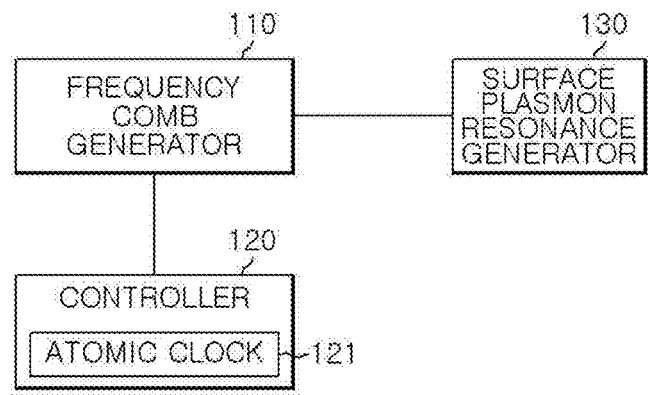
FIG. 1 is a conceptual diagram illustrating a structure of a photon generator according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, embodiments of the inventive concept will be described in detail with reference to the accompanying drawings so that those of ordinary skill in the art may easily implement the embodiments. In this regard, the inventive concept may have different forms and should not be construed as being limited to the descriptions set forth herein.

Hereinafter, embodiments of the inventive concept will be described in detail with reference to the accompanying drawings. The attached drawings for illustrating embodiments of the inventive concept are referred to in order to gain a sufficient understanding of the inventive concept, the merits thereof, and the objectives accomplished by the implementation of the inventive concept. The inventive concept may, however, be embodied in many different forms and should not be construed as being limited to the embodiments set forth herein; rather, these embodiments are provided such that this disclosure will be thorough and complete, and will fully convey the inventive concept to those of ordinary skill in the art.

The terms used herein are to describe the embodiments and are not intended to limit the scope of the inventive concept. As used herein, the singular forms "a", "an", and "the" are intended to include the plural forms as well, unless the context clearly indicates otherwise.

It will be understood that the terms such as "comprise", "include", and "have" used herein specify the presence of stated steps, operations, components, and/or elements but do not preclude the presence or addition of one or more other steps, operations, components, and/or elements.

Hereinafter, embodiments of the inventive concept will be described in detail with reference to the accompanying drawings.

FIG. 1 is a conceptual diagram illustrating a structure of a photon generator using a plasmonic frequency comb according to an embodiment.

A photon generator according to the inventive concept may include a frequency comb generator 110, a controller 120, and a surface plasmon resonance generator 130.

The frequency comb generator 110 may be configured to generate a frequency comb of a predetermined frequency band. For example, the range of a frequency spectrum band included in the frequency comb may include a wavelength band of 600 nm to 1200 nm or a wavelength band of 700 nm to 1000 nm, but is not limited thereto and may include various wide ranges.

The controller 120 may adjust the spectrum and the light quantity of an optical comb generated by the frequency comb generator 110, and may be particularly configured to implement the frequency stabilization of an optical frequency.

For example, the controller 120 may be configured to frequency-lock an optical frequency generated by the frequency comb generator 110 to an atomic frequency standard, and for this purpose, the controller 120 may include an atomic clock. For example, the atomic clock may include a cesium atomic clock and may also include a hydrogen major or optical clock that may operate as a reference frequency source. The atomic clock may operate as a standard that may be used as a reference value of time and length standard.

When the controller 120 locks a laser or optical frequency of the frequency comb generator 110 to an atomic clock 121, the frequency comb generator 110 may generate an optical frequency stabilized to the atomic clock 121 according to the atomic frequency standard and the stabilized optical frequency may be utilized in the high-accuracy standard measurement technology.

Also, the surface plasmon resonance generator 130 may be configured to generate a surface plasma resonance state or a surface plasmon resonance state of the optical frequency. For example, the surface plasmon resonance generator 130 may include a nanohole array film having a nanohole array structure including a plurality of nanoholes, and the nanohole array film may be arranged to be perpendicular to a light incidence direction. The nanohole array structure will be described below in detail with reference to the drawings.

In this manner, the accuracy of various conventional sensor measurement technologies may be greatly improved by combining a plasmonic technology of inducing a surface plasmon and a technology of applying a stabilized optical frequency technology by using a stabilized optical frequency of an atomic clock. Also, since the frequency stability of surface plasmonics may be greatly improved, it may be applied to biosensors, surface plasmon resonance (SPR) sensors, and other standard optical measurement technologies.

Figure 2:
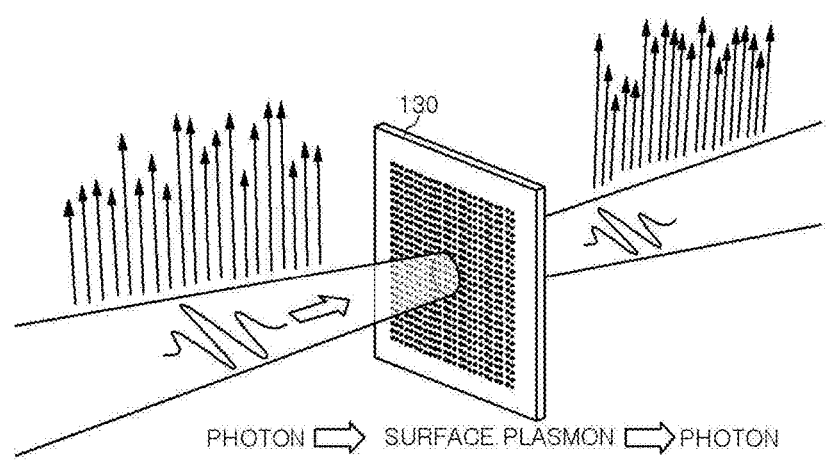
FIG. 2 is a conceptual diagram illustrating a function of a surface plasmon resonance generator according to an embodiment.

FIG. 2 is a conceptual diagram illustrating a function of a surface plasmon resonance generator according to an embodiment.

Referring to FIG. 2, photon-plasmon conversion of a frequency comb may be implemented by a surface plasmon resonance generator having a nanohole array structure. For example, an extraordinary optical transmission (EOT) phenomenon may be induced by a metal film having a nanohole array structure, and a frequency comb may pass through a metal film of a surface plasmon resonance generator by the EOT.

The nanoscale diameter of each hole of the nanohole array structure may prevent light passing therethrough based on classical optics, and the surface plasmon-mediated tunneling effect of a nanohole array may significantly improve optical transmittance.

For a new combination of a frequency comb and surface plasmon resonance, it is necessary to verify that the frequency comb may maintain its property and performance under plasmonic resonance. According to the inventive concept, when a frequency comb passes through a surface plasmon resonance generator, the frequency comb may be converted from a photonic form to a plasmonic form and then reconverted from the plasmonic form to the photonic form without significant degradation in frequency position, stability, and linewidth. These experiment results will be described in more detail with reference to FIG. 5.

Thus, according to the inventive concept, by implementing a light generator or a photon generator by combining a frequency comb and surface plasmon resonance, the superior performance of well-defined frequency combs may be applied to various biosensors, surface plasmon resonance (SPR) sensors, nanoplasmonic spectroscopy, coherent quantum metrology, and subwavelength photonic circuits.

Figure 3A:
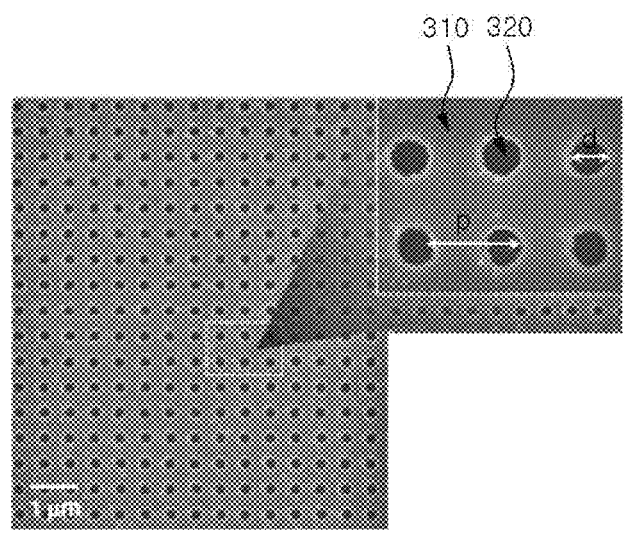
FIGS. 3A and 3B are diagrams illustrating a structure of a surface plasmon resonance generator according to an embodiment.
Figure 3B:
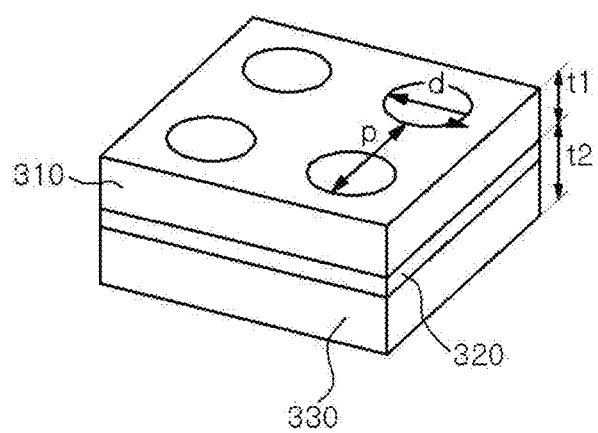

FIGS. 3A and 3B are diagrams illustrating a structure of a surface plasmon resonance generator according to an embodiment.

Referring to FIG. 3A illustrating a scanning electron microscope (SEM) image representing a plan view of a nanohole array structure of a plasma resonance generator, the surface plasmon resonance generator may include a nanohole array film having a nanohole array structure including a plurality of nanoholes, and the nanohole array film may be arranged to be perpendicular to a light incidence direction and may have an array structure including a plurality of nanoholes.

The property of extraordinary optical transmission (EOT) may be influenced, for example, by the nanohole array structure, materials, and the pitch between holes. For example, the nanohole array may include a metal layer formed on a substrate, and the metal layer may include a plurality of circular holes. Herein, for example, a metal layer may include gold, and the metal layer may be formed on a substrate including a quartz layer 330 coated with an indium tin oxide (ITO) layer 320 as illustrated in FIG. 3B.

Referring to FIG. 3B illustrating a perspective view of a surface plasmon resonance generator, with regard to the numerical values of a nanohole array structure, a diameter "d" of a circular hole may have a value of 150 nm to 250 nm, for example, about 200 nm, and a pitch "p" between a plurality of circular holes may have a value of 500 nm to 550 nm, for example, about 530 nm.

Also, a thickness t1 of a metal layer 310 including gold may be 80 nm to 120 nm, for example, about 100 nm, and a thickness t2 of the quartz layer 330 coated with the ITO layer 320 may be 20 nm to 30 nm, for example, about 25 nm.

The nanohole array structure may be designed to have the maximum optical transmittance at a wavelength of, for example, 840 nm, and the detailed experiment results thereof will be described below with reference to FIG. 5. The nanohole array structure, for example, at least one numerical value among the diameter of a circular hole, the pitch between circular holes, the thickness of a metal layer, and the thickness of a substrate may change according as the wavelength having the maximum optical transmittance changes, and inversely, the wavelength having the maximum optical transmittance may change according as the nanohole array structure changes.

Figure 4:
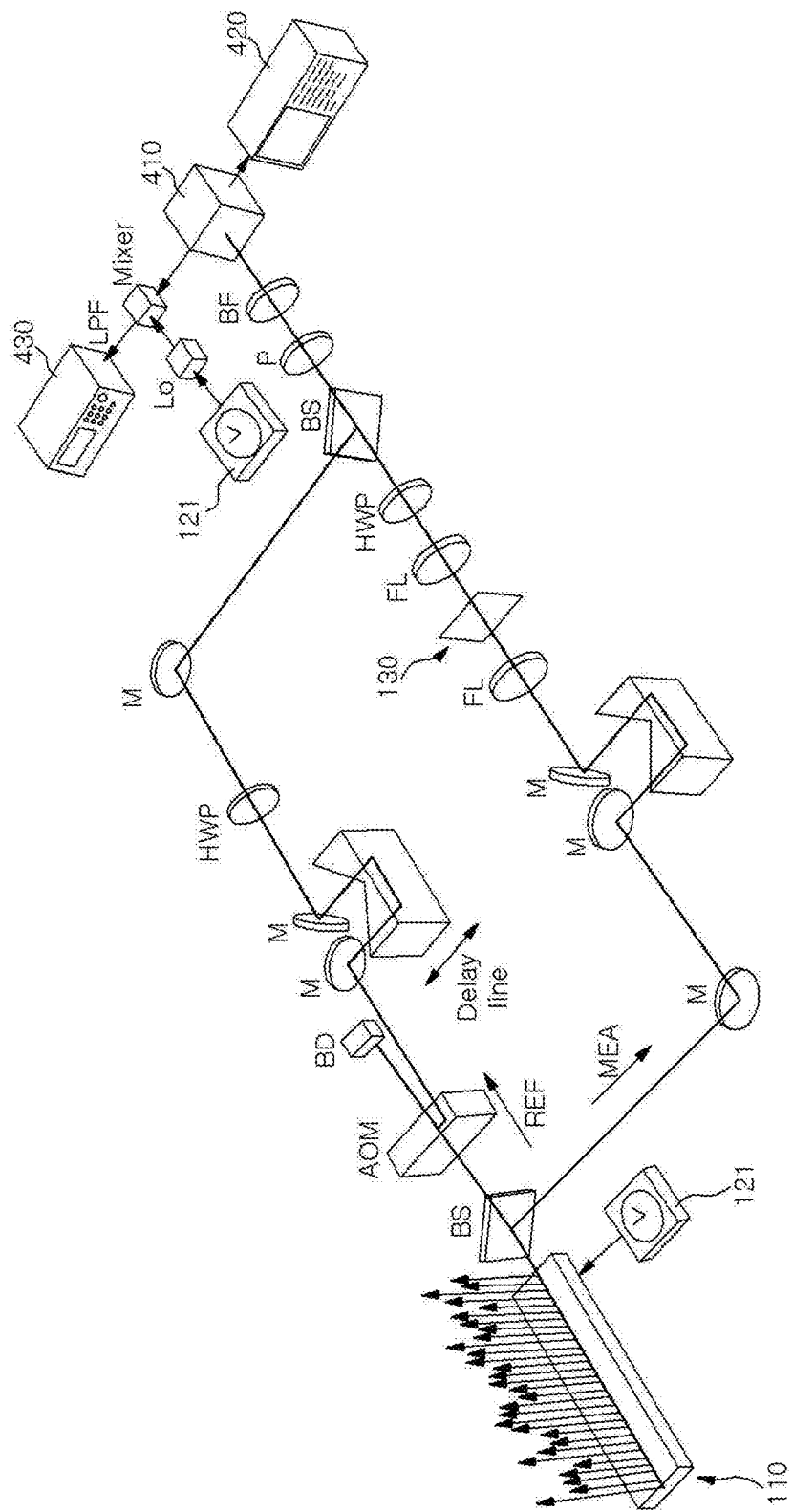
FIG. 4 illustrates a system for an experiment to confirm that a surface plasmon operates at a frequency stabilized to an atomic clock according to an embodiment.

FIG. 4 illustrates a system for an experiment to confirm that a surface plasmon operates at a frequency stabilized to an atomic clock according to an embodiment.

The system illustrated in FIG. 4 may perform an experiment to verify that the performance and characteristics of the frequency comb may be maintained through photon-surface plasmon conversion based on plasmon resonance. Referring to FIG. 4, the system may include optical components of a beam splitter BS, a mirror M, an acousto-optic modulator AOM, a beam dumper BD, a focusing lens FL, a half-wave plate HWP, a local oscillator LO, a low-pass filter LPF, and a polarizer P; and the components and a combination thereof may be partially modified.

First, the frequency comb generator 110 may generate a frequency comb having a predetermined size at each frequency and a predetermined frequency band, and the frequency comb may have a stabilized optical frequency locked to the atomic clock 121. The generated frequency comb may propagate through each of a measurement beam path MEA propagating through the surface plasmon resonance generator 130 and a reference beam path REF that is a path where the surface plasmon resonance generator 130 does not exist.

For example, the frequency comb propagating through the measurement beam path MEA may experience photon-to-surface plasmon conversion and surface plasmon-to-photon conversion through the surface plasmon resonance generator 130 including a metal film having a nanohole array as described with reference to FIGS. 2 and 3, while the reference beam propagating through the reference beam path REF may propagate in the form of a unique frequency comb without photo-plasmon conversion.

The frequency combs propagating along the two paths may be combined and monitored by a photodetector 410, and the photodetector 410 may be, for example, an avalanche photodetector. The characteristics of the plasmonic frequency comb propagating through the measurement beam path MEA may be analyzed by an RF spectrum analyzer 420 and a frequency counter 430. The experiment results analyzed by the system experiment apparatus of FIG. 4 will be described below with reference to FIG. 5.

FIGS. 5A, 5B, 5C, and 5D are diagrams illustrating analysis results of surface plasmon characteristics according to an embodiment.

Figure 5A:
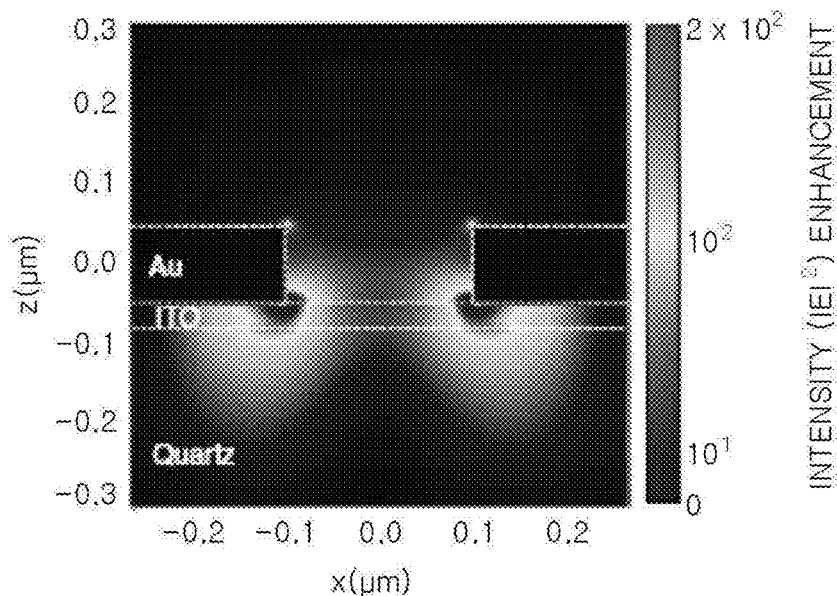
FIGS. 5A, 5B, 5C, and 5D are diagrams illustrating analysis results of surface plasmon characteristics according to an embodiment.
Figure 5B:
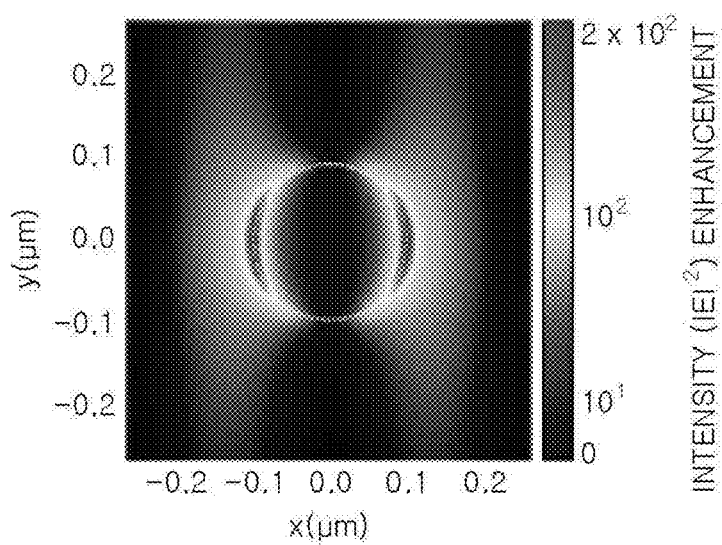

FIG. 5A illustrates a calculated intensity distribution of a plasmonic sample viewed from the side, and FIG. 5B illustrates a calculated intensity distribution on an interface plane between a metal layer and a substrate. FIG. 5A illustrates a side view of a metal layer 310 including gold and a quartz substrate 330 coated with an indium tin oxide (ITO) 320, and FIG. 5B illustrates a top view of an interface between a metal layer 310 including gold and an indium tin oxide (ITO) 320.

Referring to the experiment results of FIGS. 5A and 5B, in a repetitive aperture structure of the surface plasmon resonance generator 130, an electric field near a circular hole formed in the metal layer may be considerably enhanced by the surface plasmon and thus optical energy may be transmitted through the circular hole.

Figure 5C:
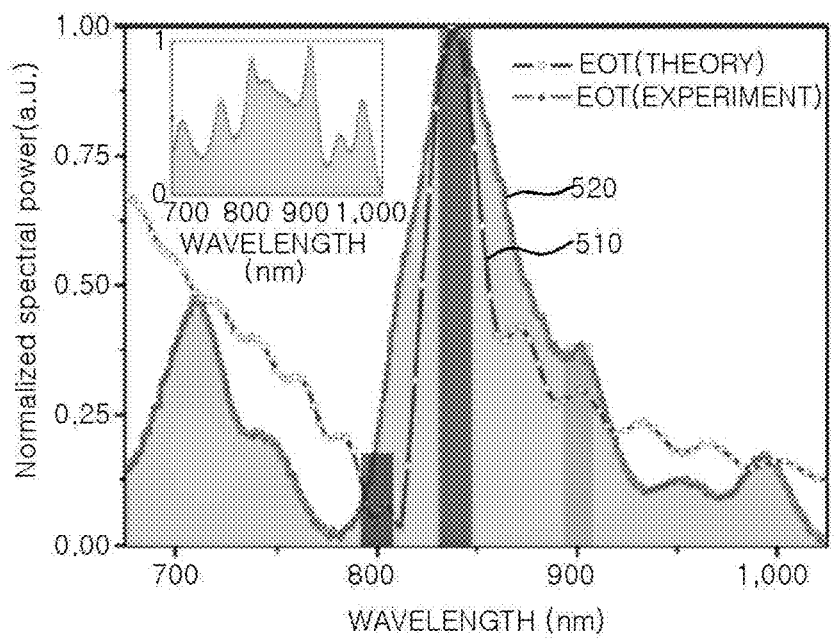

FIG. 5C is a graph illustrating that the transmitted optical spectrum and the calculation result of numerical analysis through a finite-difference time-domain (FDTD) simulation method are equal to each other and thus the numerical analysis result is valid.

Referring to FIG. 5C, a small wavelength graph shown at the left top side represents an initial spectrum of the frequency comb, the result of the entire wavelength graph represents a power spectrum of extraordinary optical transmission (EOT) through surface plasmon resonance, a line 510 represents the theoretical result, and a line 520 represents the experiment result.

As illustrated in the graph of FIG. 5C, the theoretical result and the experiment result are substantially equal to each other without a great difference, and particularly in the present experiment, the characteristics of normalized spectral power values represented by bars at wavelengths of 800 nm, 840 nm, and 900 nm corresponding to a selected frequency spectrum of the frequency comb may be equal to each other.

Basically, the frequency comb may be adversely affected by phase and frequency noise when passing through a medium of optical fiber or air exposed to an environment change such as a vibration, a temperature change, and a humidity change. Thus, it may be very important to perform an operation for monitoring and compensating for temporal and spectral dispersion, phase noise, and frequency noise generated in a propagation medium in frequency comb utilization. However, in the case of utilizing a plasmonic frequency comb according to the inventive concept, since plasmonic mode conversion may not adversely affect the noise occurrence and the frequency accuracy of a frequency comb, the dispersion and noise effect in the case of using a conventional frequency comb may be considerably reduced.

Figure 5D:
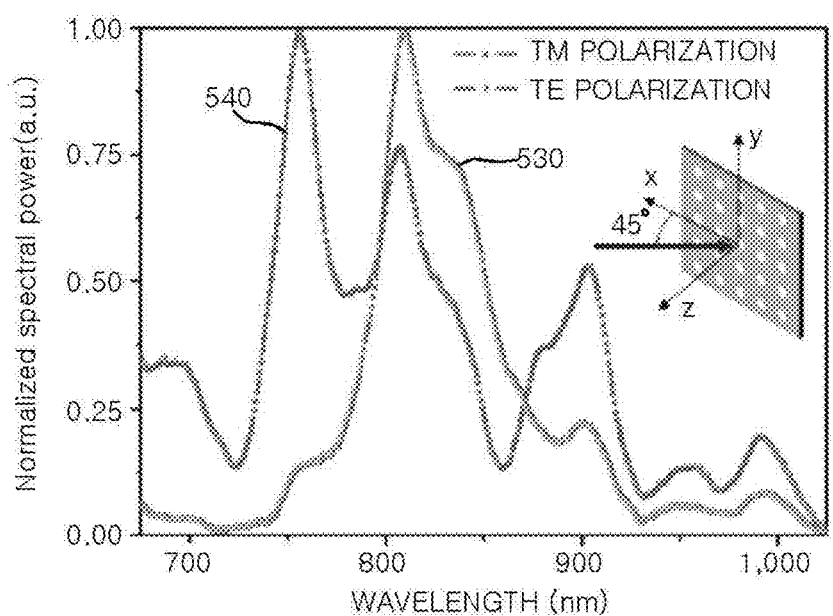

FIG. 5D is a graph illustrating the characteristics of a polarization-dependent optical transmission spectrum in the case of nanohole array film penetration when the incidence angle of light is 45 degrees. A graph 530 of FIG. 5D illustrates the experiment result of a frequency comb of a transverse electric (TE) polarized wave, that is, a vertically polarized wave having a vertical polarization with a vibration direction perpendicular to the incidence plane, and a graph 540 of FIG. 5D illustrates the experiment result of a frequency comb of a transverse magnetic (TM) polarized wave, that is, a horizontally polarized wave having a horizontal polarization with a vibration direction parallel to the incidence plane.

Referring to FIG. 5D, in the case of TE polarization, similarly to the case of FIG. 5C of the light incidence angle being 90 degrees, a peak value may occur at a wavelength of about 840 nm and thus it may have similar spectral power characteristics regardless of the light incidence angle; while in the case of TM polarization, unlike the experiment result of FIG. 5C, spectral power characteristics may be different and a peak value may occur in a different frequency band. In this manner, from the experiment results having different characteristics of TE polarization and TM polarization, it may be seen that the optical transmission of the plasmonic frequency comb may be characterized by the plasmonic EOT and the classical optical diffraction theory may not be applied thereto.

According to the inventive concept, it is possible to greatly improve the accuracy of various conventional sensor measurement technologies by combining a technology of inducing a surface plasmon and a technology of applying a stabilized optical frequency technology to a plasmonic technology by using an optical frequency stabilized to an atomic clock.

Also, according to the inventive concept, it is possible to provide a photon generator including an apparatus for inducing a surface plasmon by using a stabilized optical frequency and a sensor including the same.

Also, according to the inventive concept, it is possible to utilize an optical frequency in a high-accuracy standard measurement technology by locking a laser or optical frequency based on an atomic clock having high stability and accuracy.

Also, according to the inventive concept, it is possible to apply to biosensors, surface plasmon resonance (SPR) sensors, and other standard optical measurement technologies by greatly improving the frequency stability of surface plasmonics by utilizing an optical frequency stabilized to an atomic clock for surface plasmon induction.

Effects of the inventive concept are not limited to the above-mentioned effects, and unmentioned other effects may be clearly understood from the following description by those of ordinary skill in the art.

Although certain embodiments of photon or laser generating apparatuses and photon generating methods using plasmonic frequency combs according to the inventive concept have been described above, they are merely examples and the inventive concept is not limited thereto and should be construed as having the maximum possible scope according to the basic idea described herein. Those of ordinary skill in the art may also implement other undescribed types of patterns by combining or substituting the described embodiments without departing from the spirit and scope of the inventive concept. The scope of the inventive concept may be defined not by the above detailed descriptions but by the following claims, and all differences within the equivalent scope thereof may be construed as being included in the scope of the inventive concept.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

What is claimed is:

1. A photon generator comprising:
a frequency comb generator configured to generate a frequency comb of a predetermined frequency band;
a controller configured to perform frequency locking for frequency stabilization of an optical frequency generated by the frequency comb generator; and
a surface plasmon resonance generator configured to generate a surface plasmon resonance state of the frequency comb for photon-plasmon conversion of a frequency comb.

2. The photon generator of claim 1, wherein the surface plasmon resonance generator comprises a nanohole array film having a nanohole array structure comprising a plurality of nanoholes.

3. The photon generator of claim 2, wherein the nanohole array film comprises a metal layer formed on a substrate, and the metal layer comprises a plurality of circular holes.

4. The photon generator of claim 3, wherein the metal layer comprises gold, and the substrate comprises a quartz layer coated with indium tin oxide.

5. The photon generator of claim 3, wherein a diameter of each of the plurality of circular holes is about 150 nm to about 250 nm, and a pitch between the plurality of circular holes is about 500 nm to about 550 nm.

6. The photon generator of claim 3, wherein a thickness of the metal layer is about 80 nm to about 120 nm, and a thickness of the substrate is about 20 nm to about 30 nm.

7. A biosensor comprising the photon generator of claim 2.

8. The photon generator of claim 1, wherein the controller is configured to frequency-lock the optical frequency generated by the frequency comb generator to an atomic frequency standard.

9. The photon generator of claim 1, wherein the controller comprises an atomic clock.

10. A biosensor comprising the photon generator of claim 1.

11. A photon generating method comprising:
generating a frequency comb of a predetermined frequency band;
frequency-locking an optical frequency to an atomic frequency standard for frequency stabilization of the optical frequency generated by a frequency comb generator; and
generating a surface plasmon resonance state of the frequency comb by a surface plasmon resonance generator for photon-plasmon conversion of a frequency comb.

12. The photon generating method of claim 11, wherein the generating of the surface plasmon resonance state comprises the frequency comb passing through a nanohole array film having a nanohole array structure comprising a plurality of nanoholes.

13. The photon generating method of claim 12, wherein the nanohole array film comprises a metal layer formed on a substrate, and the metal layer comprises a plurality of circular holes.

14. The photon generating method of claim 13, wherein the metal layer comprises gold, and the substrate comprises a quartz layer coated with indium tin oxide.

15. The photon generating method of claim 13, wherein a diameter of each of the plurality of circular holes is about 150 nm to about 250 nm, and a pitch between the plurality of circular holes is about 500 nm to about 550 nm.

16. The photon generating method of claim 13, wherein a thickness of the metal layer is about 80 nm to about 120 nm, and a thickness of the substrate is about 20 nm to about 30 nm.

17. The photon generating method of claim 11, wherein the frequency comb is reconverted from a surface plasmonic mode to a photonic mode after being converted from the photonic mode to the surface plasmonic mode by the surface plasmon resonance generator.

* * * * *